United States Patent [19]

Decaudin et al.

[11] Patent Number: 4,701,564

[45] Date of Patent: Oct. 20, 1987

[54] PROCESS FOR THE PREPARATION OF BROMINATED DERIVATIVES OF DIPHENYL ETHER

[75] Inventors: Robert Decaudin, Pelissanne; Bernard Gurtner, Grenoble; Andre Gagnieur, Rochetaille Sur Saone, all of France

[73] Assignee: Atochem, Puteaux, France

[21] Appl. No.: 881,873

[22] Filed: Jul. 3, 1986

[30] Foreign Application Priority Data

Jul. 3, 1985 [FR] France .................. 85 10161

[51] Int. Cl.$^4$ ............... C07C 41/22; C07C 43/025
[52] U.S. Cl. ............................................ 568/639
[58] Field of Search ................................ 568/639

[56] References Cited

U.S. PATENT DOCUMENTS

| | | | |
|---|---|---|---|
| 2,022,634 | 11/1935 | Britton et al. | 568/639 |
| 3,232,959 | 2/1966 | Hahn | 568/639 X |
| 3,760,003 | 9/1973 | Asadorian et al. | 260/613 R |
| 3,763,248 | 10/1973 | Mitchell | 260/649 D |
| 3,959,387 | 5/1976 | Brackenridge | 260/612 R |
| 4,134,925 | 1/1979 | Petersen et al. | 568/637 |
| 4,287,373 | 9/1981 | Garman et al. | 568/639 |
| 4,521,633 | 6/1985 | Pedjac | 568/639 |

FOREIGN PATENT DOCUMENTS

| | | |
|---|---|---|
| 1193510 | 10/1962 | Fed. Rep. of Germany . |
| 128749 | 12/1976 | Fed. Rep. of Germany . |
| 2319612 | 2/1977 | France . |
| 2505821 | 11/1982 | France . |
| 0124731 | 9/1980 | Japan .................. 568/639 |
| 1472383 | 1/1975 | United Kingdom . |
| 1519273 | 6/1978 | United Kingdom . |
| 2143521 | 2/1985 | United Kingdom . |

OTHER PUBLICATIONS

Chemical Abstracts 90: 103605p, p. 560 (1979).
Chem Abstracts, 91 140538 (k) (1979).
Chem Abstracts, 91 140542 (g) (1979).
Chem Abstracts, 103 37191 (j) (1985).
L. Denivelle, R. Fort, P. V. Hai, Bull. Soc. Chim. France, 1538–1543 (1960).
Chem Abstracts, 83 27887 (v) (1975).
Chem Abstracts, 87 134550 (j) (1977).
Chem Abstracts, 87 134551 (k) (1977).
Chem Abstracts, 90 103616 (t) (1979).

Primary Examiner—J. E. Evans
Attorney, Agent, or Firm—Pennie & Edmonds

[57] ABSTRACT

The invention relates to the preparation of brominated derivatives of diphenyl ether. This process includes preparing an underbrominated product and perbrominating the by-products of this reaction. This process is particularly suitable for the preparation of octabromodiphenyl ether and decabromodiphenyl ether.

20 Claims, No Drawings

PROCESS FOR THE PREPARATION OF BROMINATED DERIVATIVES OF DIPHENYL ETHER

FIELD OF THE INVENTION

The subject of the invention is a process for the preparation of brominated derivatives of diphenyl ether. It is especially concerned with the derivatives containing 8 to 10 bromine atoms per molecule, and more precisely, it aims at obtaining underbrominated products and upgrading the by-products to perbrominated products.

In the present document and for simplification, diphenyl ether containing 10 bromine atoms will be called "perbrominated" and diphenyl ether containing less than 10 bromine atoms will be called "underbrominated".

DESCRIPTION OF THE INVENTION

The process according to the invention, which employs diphenyl ether, a bromination catalyst, an organic solvent and a brominating agent, is characterized in that it consists in:
  (a) gradual addition of the brominating agent to a mixture comprising diphenyl ether, the brominating catalyst and the organic solvent, the brominating agent being used in a quantity corresponding closely to the stoichiometry, based on bromine, of the underbrominated product sought;
  (b) allowing the reaction to proceed until underbrominated diphenyl ether (I) impregnated with the solvent on the one hand and crude solvent (II) containing underbrominated diphenyl ether (III) on the other are obtained;
  (c) adding the bromination catalyst to the crude solvent (II) and gradual addition to this mixture of the brominating agent in molar excess in relation to the stoichiometry of the perbromination of underbrominated diphenyl ether (III);
  (d) raising the temperature of the medium obtained in c to the reflux temperature of the organic solvent and maintaining it at this temperature until the perbromination reaction is complete;
  (e) after cooling, collecting perbrominated diphenyl ether (IV) containing some solvent on the one hand, and the solvent on the other;
  (f) drying the underbrominated diphenyl ether (I) and the perbrominated diphenyl ether (IV) obtained in b and e respectively.

In the text that follows, the terms "phase" or "stage" will be used, without discrimination, to denote the different operations a to f.

The invention employs diphenyl ether as the starting product

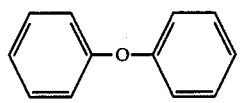

It goes without saying that the invention extends to mixtures containing such a product and especially to mixtures of this product with weakly brominated diphenyl ethers, that is to say, containing less than 8 bromine atoms per molecule.

In the present document, the term used for each type of product (catalyst, brominating agent, solvent) will denote, without discrimination, a single product or a mixture of several products of the same type.

The brominating agent can be chosen from products which are known for the bromination of aromatic rings. This agent advantageously consists of bromine itself.

Various kinds of catalysts have been described in the literature and can be employed in the present process. U.S. Pat. No. 4,287,373 can be referred to on this matter. Although certain metals such as aluminium can be used, aluminium halides and especially a halide chosen from the group consisting of aluminium chloride or bromide will advantageously be chosen. The catalyst may be in the form of particles or agglomerates, the mean diameter of particles may range from 0.05 to 15 mm, these values being given by way of information only. The nonmetallic catalyst may be of an amorphous or a crystalline structure.

In the present process, the bromination reactions are carried out in an organic solvent medium. In general, the solvent can be chosen from halogenated hydrocarbons. Among these, hydrocarbons containing one carbon atom and substituted with bromine and/or chlorine will be recommended, preference being given to methylene bromide.

In the process according to the invention, the different agents and reagents listed above are advantageously employed in the following proportions:
  with regard to the bromination catalyst, the quantity may amount to 2 to 20% by mole of the catalyst, per mole of diphenyl ether
  with regard to the solvent, 1 to 6 moles of the solvent per mole of diphenyl ether started with in the process may be used
  with regard to the brominating agent, the molar excess in relation to the stoichiometry of perbromination of under brominated diphenyl ether (III) -phase c - may go up to 10% and is preferably between 3 and 8%, these values being calculated on the basis of the stoichiometry of perbromination of underbrominated diphenyl ether and increased where appropriate, by the additional diphenyl ether mentioned later.

The phases a, b, c and e of the process of the invention may be performed at room temperature or at the very least within the range from 20° to 50° C. The temperature for carrying out phase b of the process depends on the solvent used. Thus, in the specific case of methylene bromide, and for a reaction carried out at atmospheric pressure, the temperature will be of the order of 95°–99° C.

As for the temperature of drying of phase f of the process, it depends naturally on the nature of the products formed, the solvent used and the conditions of the drying itself. In general, this temperature is greater than 50° C. and less than the melting point of the underbrominated or perbrominated compound sought.

In the process according to the invention, stage a consists in the gradual introduction of the brominating agent into the mixture comprising diphenyl ether, the bromination catalyst and the organic solvent. It is advantageous to prepare this mixture in the first place by incorporation of the diphenyl ether and the catalyst into the organic solvent, with stirring. The introduction of the brominating agent is carried out by pouring it, in a continuous or discontinuous manner, into the said mixture. In general, the duration of this pouring operation varies between 1 and 10 hours; these values should be regarded as an order of magnitude only. The pouring itself is followed by a phase called the reaction phase allowing the latter to proceed and to come to an end; the duration of this phase (phase b of the process) may be up to a few hours, for example up to 4 hours.

The actual pouring phase as well as the reaction phase are carried out preferably with stirring of the medium.

The obtention of the underbrominated diphenyl ether (I) and the crude solvent (II) (phase b of the process) is advantageously preceded by a treatment of purification of the medium and liquid/solid separation. This involves operations consisting essentially in: deactivation of the catalyst, for example by adding water, acidified if appropriate, followed by a destruction of the residual brominating agent (especially $Br_2$), for example using sodium metabisulphite or hydrazine, if required, a phase consisting in decantation and removal of the supernatant aqueous phase which essentially contains the catalyst and, finally, operations of washing with water followed by draining which make it possible to recover the underbrominated diphenyl ether (I) impregnated with the solvent on the one hand, and the crude organic solvent (II) containing another fraction of underbrominated diphenyl ether (III) in solution on the other.

With regard to phase c of the process and according to a variation, diphenyl ether is also added to the crude solvent (II) in a quantity which may amount to up to 100% (in moles) of the underbrominated diphenyl ether (III). Solvent may also be added within the limits of the proportions indicated previously.

The maintenance of the solvent of phase d at the reflux temperature advantageously lasts between 30 minutes and 2 hours.

The recovery of the perbrominated diphenyl ether (IV) containing some solvent on the one hand and the solvent according to phase e of the process on the other is also advantageously preceded, mutatis mutandis, by all or a part of the treatments of purification and solid/liquid separation mentioned above. The cooling mentioned in this phase e means returning to the medium to room temperature or, more commonly to 20°-50° C.

The process of the invention may comprise only a sequence of stages a to e defined as above only; the drying f of the underbrominated diphenyl ether (II) may be carried out at any time after stage b.

According to an especially useful variation of the process of the invention, operations a and b are repeated n times (n may be between 1 and 5 for example) before c and the following operations by employing the crude solvent II of stage b as the "organic solvent" and bringing the quantity of organic solvent to that provided for in stage a by adding sufficient quantity of fresh solvent to the crude solvent (II).

The preparation of underbrominated compounds generally gives, besides the product sought, a solution containing a significant proportion of underbrominated product, for example of the order of 15 to 20% or even higher. Multiple recycling of this solution enables the loss of the said product to be limited but to the detriment of its quality, especially with regard to colour. The process according to the invention makes it possible to upgrade the underbrominated product which is thus present in the form of a solution by perbrominating it, the perbrominated products thus obtained themselves being valuable products, especially as fireproofing agents.

Purely by way of information, this process makes it possible to brominate diphenyl ether with a high yield (molar yield of underbrominated and perbrominated products recovered relative to the diphenyl ether used at start greater than 90% or even 95%).

The following examples illustrate the invention:

EXAMPLE 1

(a) into a reactor containing 435 g of methylene bromide
85 g of diphenyl ether, and
10 g of aluminum chloride are introduced, with stirring.

640 g of bromine are poured over 3 hours into the reaction mixture above at room temperature (25° C.). After maintaining it at the same temperature (25° C.) for a further period of 2 hours, the catalyst is destroyed by adding 100 g of water.

After destruction of the traces of residual bromine with an aqueous solution of hydrazine, decantation and removal of the supernatant aqueous phase containing the deactivated catalyst are carried out. Three operations of washing with water and decantation are then carried out. The organic phase is filtered and drained.

The following are thus recovered:
a phase of $A_1$ of underbrominated diphenyl ether impregnated with the solvent
a phase $B_1$ which consists of the solvent containing dissolved underbrominated diphenyl ether.

(b) the phase $A_1$ is dried (70° C. under vacuum - 3 hours) and 287.3 g of underbrominated diphenyl ether with 8.2 bromine atoms per molecule on average are collected.

39.6 g of methylene bromide, 12.6 g of diphenyl ether and 5.4 g of aluminium chloride are added to an aliquot part of phase $B_1$ (271 g) containing 26.9% of the dissolved product with 7.43 bromine atoms per molecule, with stirring and at room temperature.

167 g of bromine are poured over 1 hour into this mixture at 23° C.

The whole mixture is brought to boiling point and maintained at the reflux temperature of the solvent for 1 hour.

After purification and separation treatments mentioned in a above.
a phase $A_2$ of perbrominated diphenyl ether impregnated with the solvent, and
a phase $B_2$ of the solvent (5.6% of the underbrominated diphenyl ether solvent of an average degree of bromination of 9.5) are collected.

After drying phase $A_2$, 141.7 g of perbrominated diphenyl ether are collected.

EXAMPLE 2

(a) into a reactor containing 1,092 kg of methylene bromide
209 kg of diphenyl ether, and
25 kg of aluminium chloride are introduced.

1,608 kg of bromine are poured over 5 h 30 min at room temperature and maintained at this temperature (25° C.) for 2 hours.

The purification/separation treatments of Example 1 to obtain a phase $A_1$ (underbrominated diphenyl ether impregnated with the solvent) and a phase $B_1$ (solvent containing dissolved underbrominated derivatives) are carried out.

(b) to solution $B_1$, containing 20.4% by weight of the dissolved product (average degree of bromination 7.4)
110 kg of methylene bromide,
209 kg of diphenyl ether, and
25 kg of aluminium chloride are added.

1,614 kg of bromine are poured over 5 h 30 min into this mixture at 25° C. and maintained at 25° C. for 2 hours.

After the treatments mentioned above, a phase $A_2$ (underbrominated diphenyl ether impregnated with the solvent) and a phase $B_2$ (solvent containing the dissolved brominated derivative) are collected.

(c) to solution $B_2$ (24.6% by weight of dissolved product, average degree of bromination of 7.4)
115 kg of methylene bromide,
210 kg of diphenyl ether, and
25 kg of aluminum chloride are added.

1,623 of bromine are poured into this mixture (25° C. for 5 h 30 min).

After the appropriate treatments
a phase $A_3$ (underbrominated diphenyl ether impregnated with the solvent), and
a phase $B_3$ (solvent containing dissolved brominated derivatives) are collected.

(d) to solution $B_3$ (24.5% of dissolved products average degree of bromination 7.4)
40.1 kg of diphenyl ether, and
20 kg of aluminum chloride are added.

580 kg of bromine are poured over 2 hours into this mixture at 25° C.

After heating to boiling point, maintaining at this temperature for 1 hour and cooling, followed by the purification/separation treatments mentioned above
a phase $A_4$ consisting of perbrominated diphenyl ether impregnated with the solvent
a solvent $B_4$ phase (2.6% by weight of dissolved underbrominated diphenyl ether) are collected.

After drying phases $A_1$, $A_2$, $A_3$ and $A_4$
2,460 kg of underbrominated diphenyl ether (average degree of bromination 8.1), and
578 of perbrominated diphenyl ether are obtained.

The loss of diphenyl ether in solvent $B_4$ is less than 2%.

EXAMPLE 3

The procedure of Example 2 is repeated by preparing four underbrominated diphenyl ether phases (instead of 3) and a perbrominated diphenyl ether phase, using the reagents in the following proportions:

| Phase | $A_1$ | $A_2$ | $A_3$ | $A_4$ | $A_5$ |
|---|---|---|---|---|---|
| Diphenyl ether kg | 194 | 207 | 207 | 237 | 63.8 |
| Methylene bromide kg | 1,092 | 105 | 120 | 110 | 105 |
| AlCl$_3$ kg | 25 | 25 | 25 | 30 | 24.2 |
| Bromine kg | 1,503 | 1,594 | 1,606 | 1,860 | 800 |
| Solution $B_n$ | — | $B_1$ | $B_2$ | $B_3$ | $B_4$ |

(Solution $B_n$ denotes the solution from the previous phase employed in the operation concerned)

After drying phases $A_1$, $A_2$, $A_3$, $A_4$ and $A_5$
3,640 kg of underbrominated diphenyl ether (average degree of bromination 8.1), and
650 kg of perbrominated diphenyl ether are obtained.

The final solution $B_5$ contains 5.75% of dissolved underbrominated diphenyl ether.

The total loss of diphenyl ether in solvent $B_5$ is less than 2%.

The yield (in moles) of the underbrominated and perbrominated products, relative to the diphenyl ether used at start, is greater than 96%.

We claim:

1. Process for the preparation of underbrominated diphenyl ether products and upgrading these products to perbrominated diphenyl ether products, using diphenyl ether, a bromination catalyst, an organic solvent and a brominating agent, characterized that said process comprises:

(a) gradually adding a brominating agent to a first mixture comprising diphenyl ether, a bromination catalyst, and an organic solvent, the brominating agent being used in a quantity corresponding closely to the stoichiemetry, based on bromine, of the underbrominated diphenyl ether product sought;

(b) allowing the reaction to proceed to obtain a first solution of underbrominated diphenyl ether(I) impregnated with the organic solvent, and a second solution of crude solvent (II) containing underbrominated diphenyl ether (III);

(c) adding further bromination catalyst to the second solution to form a second mixture followed by the gradual addition to this second mixture of further brominating agent in molar excess in relation to the stoichiometry of the perbromination of the underbrominated diphenyl ether (III) to form a reaction medium;

(d) raising the temperature of the reaction medium obtained in c to the reflux temperature of the organic solvent and maintaining this temperature until the perbromination reaction is complete;

(e) after cooling, collecting the perbrominated diphenyl ether product (IV); and (f) drying the underbrominated diphenyl ether product (I) and the perbrominated diphenyl ether product (IV) obtained in b and e respectively.

2. Process according to claim 1, characterized in that it includes repeating n times operations a and b before c and the following operations, n being between 1 and 5, by employing the crude solvent II of stage b as the organic solvent and bringing the quantity of organic solvent up to that provided for in stage a by adding sufficient quantity of fresh solvent to the crude solvent II.

3. Process according to claim 1, characterized in that in phase c, diphenyl ether is added in a quantity which may amount up to 100% (in moles) of the underbrominated diphenyl ether (III) to the crude solvent (II).

4. Process according to claim 1, characterized in that the brominating agent is bromine.

5. Process according to claim 1, characterized in that the bromination catalyst is an aluminium halide chosen from the group consisting of aluminium chloride and bromide.

6. Process according to claim 1, characterized in that the organic solvent is a halogenated hydrocarbon.

7. Process according to claim 6, characterized in that the solvent is methylene bromide.

8. Process according to claim 1, characterized in that the quantity of catalyst amounts to 2 to 20% (in moles) of the catalyst per mole of diphenyl ether.

9. Process according to claim 1, characterized in that the solvent is employed in phase a at a rate of 1 to 6 moles of the solvent per mole of diphenyl ether used at start in the process.

10. Process according to claim 1, characterized in that the molar excess of the brominating agent, in relation to the stoichiometry of perbromination of the underbrominated diphenyl ether (III) may go up to 10%, these values being calculated on the basis of the stoichiometry of the perbromination of the underbrominated diphenyl ether, and increased where appropriate, by the addition of diphenyl ether.

11. Process for the preparation of an octabromodiphenyl ether product and upgrading this product to decabromodiphenyl ether, using diphenyl ether, a bromination catalyst, an organic solvent and a brominating agent, which process comprises:
  (a) gradual adding the brominating agent to a first mixture comprising diphenyl ether and the organic solvent, the brominating agent being used in a quantity corresponding closely to the stoichiometry, based on bromine, of octabrominated diphenyl ether (I);
  (b) allowing the reaction to proceed until octabrominated diphenyl ether (I) impregnated with the organic solvent, and a crude solvent (II) solution containing octabrominated diphenyl ether (III) are obtained;
  (c) adding further bromination catalyst to the crude solvent (II) solution to form a second mixture and gradually adding to this second mixture further brominating agent in molar excess to the stoichiometry needed for the perbromination of octabrominated diphenyl ether (III) to form a reaction medium;
  (d) raising the temperature of the reaction medium obtained in c to the reflux temperature of the organic solvent and maintaining this temperature until the perbromination reaction is complete;
  (e) after cooling, collecting decabrominated diphenyl ether (IV); and
  (f) drying the underbrominated diphenyl ether (I) and the decabrominated diphenyl ether (IV) obtained in b and e respectively.

12. Process according to claim 1, characterized in that the phase a, b, c and e of the process are carried out at room temperature from 20° to 50° C.

13. Process according to claim 1, characterized in that the drying temperature is between 50° C. and the melting point of the underbrominated diphenyl ether.

14. Process according to claim 1, characterized in that the duration of phase a of the process varies between 1 and 10 hours, phase b is up to about 4 hours.

15. Process according to claim 11 characterized in that in phase c, diphenyl ether is added to the crude solvent (II) in a quantity which may amount up to 100% (in moles) of the octabrominated diphenyl ether (III).

16. Process according to claim 11 wherein the bromination catalyst is bromine.

17. Process according to claim 11 wherein the organic solvent is a halogenated hydrocarbon.

18. Process according to claim 11 wherein brominating agent is an aluminum halide.

19. Process for the preparation of decabromodiphenyl ether from octabromo diphenyl ether using diphenyl ether, bromine as a bromination catalyst, a halogenated hydrocarbon as an organic solvent and an aluminum halide as a brominating agent, which process comprises:
  (a) gradual adding bromine to a first mixture comprising diphenyl ether and the halogenated hydrocarbon, the bromine being used in a quantity corresponding closely to the stoichiometry of octabrominated diphenyl ether (I);
  (b) allowing the reaction to proceed until octabrominated diphenyl ether (I) impregnated with the halogenated hydrocarbon solvent, and a crude solvent (II) solution containing octabrominated diphenyl ether (III) are obtained;
  (c) adding further bromine catalyst to the crude solvent (II) solution to form a second mixture and gradually adding to this second mixture an aluminum halide brominating agent in molar excess to the stoichiometry needed for the perbromination of octabrominated diphenyl ether (III) to form a reaction medium;
  (d) raising the temperature of the reaction medium obtained in c to the reflux temperature of the halogenated hydrocarbon solvent and maintaining this temperature until the perbromination reaction is complete;
  (e) after cooling, collecting decarbrominated diphenyl ether (IV); and
  (f) drying the underbrominated diphenyl ether (I) and the decabrominated diphenyl ether (IV) obtained in b and e respectively.

20. Process according to claim 19 wherein the aluminum halide brominating agent is aluminum chloride or aluminum bromide.

* * * * *